(12) United States Patent
Majolagbe

(10) Patent No.: US 10,646,323 B2
(45) Date of Patent: May 12, 2020

(54) TOTAL ARCH CONCEPT

(71) Applicant: W. L. Gore & Associates, Inc., Newark, DE (US)

(72) Inventor: Kehinde A. Majolagbe, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 198 days.

(21) Appl. No.: 15/698,861

(22) Filed: Sep. 8, 2017

(65) Prior Publication Data

US 2018/0071078 A1  Mar. 15, 2018

Related U.S. Application Data

(60) Provisional application No. 62/385,484, filed on Sep. 9, 2016.

(51) Int. Cl.
*A61F 2/07* (2013.01)
*A61F 2/966* (2013.01)
*A61F 2/06* (2013.01)

(52) U.S. Cl.
CPC .............. *A61F 2/07* (2013.01); *A61F 2/966* (2013.01); *A61F 2002/061* (2013.01); *A61F 2002/067* (2013.01); *A61F 2210/0014* (2013.01); *A61F 2210/0076* (2013.01); *A61F 2220/005* (2013.01); *A61F 2230/0078* (2013.01); *A61F 2250/0039* (2013.01)

(58) Field of Classification Search
CPC ...... A61F 2/06; A61F 2/07; A61F 2/82; A61F 2002/83; A61F 2250/0039
USPC .................................................. 623/1.27–1.35
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| 5,276,276 A | 1/1994 | Gunn |
| 5,919,225 A | 7/1999 | Lau |
| 6,042,605 A | 3/2000 | Martin |
| 8,858,612 B2 * | 10/2014 | Ben-Muvhar ............. A61F 2/91 623/1.11 |
| 9,597,204 B2 * | 3/2017 | Benary .................... A61F 2/07 |
| 10,058,413 B2 * | 8/2018 | Heiss ....................... A61F 2/04 |
| 2005/0055082 A1 | 3/2005 | Ben et al. |
| 2007/0055299 A1 | 3/2007 | Ishimaru |
| 2008/0194905 A1 | 8/2008 | Walsh |
| 2008/0269866 A1 | 10/2008 | Hamer |
| 2010/0049294 A1 | 2/2010 | Zukowski |
| 2013/0013051 A1 | 1/2013 | Benary |

(Continued)

FOREIGN PATENT DOCUMENTS

| | | |
|---|---|---|
| EP | 1874231 B1 | 1/2016 |
| JP | 2005-503881 A | 2/2005 |

(Continued)

OTHER PUBLICATIONS

International Search Report and Written Opinion from PCT/US2017/050607, dated Jan. 31, 2018, 10 pages.

*Primary Examiner* — Suzette J Gherbi

(57) ABSTRACT

Various aspects of the present disclosure are directed toward prosthesis that may include a first graft component and a second graft component coupled to the first graft component. The prosthesis may also include a gap or a space between the first graft component and the second graft component.

25 Claims, 6 Drawing Sheets

(56) References Cited

U.S. PATENT DOCUMENTS

| | | | |
|---|---|---|---|
| 2013/0184806 A1 | 7/2013 | Arbefeuille | |
| 2013/0204347 A1* | 8/2013 | Armstrong | A61F 2/07 623/1.13 |
| 2013/0211506 A1 | 8/2013 | Dake et al. | |
| 2013/0218257 A1* | 8/2013 | Sun | A61F 2/07 623/1.13 |
| 2014/0067041 A1* | 3/2014 | Ben-Muvhar | A61F 2/91 623/1.15 |
| 2014/0316514 A1 | 10/2014 | Zukowski | |
| 2015/0088239 A1* | 3/2015 | Ben-Muvhar | A61F 2/91 623/1.3 |
| 2015/0105851 A1* | 4/2015 | Shalev | A61F 2/07 623/1.13 |
| 2015/0216686 A1 | 8/2015 | Chakfe et al. | |
| 2016/0256169 A1 | 9/2016 | Ben-Muvhar | |
| 2017/0135807 A1* | 5/2017 | Arbefeuille | A61F 2/07 |
| 2017/0216062 A1* | 8/2017 | Armstrong | A61F 2/07 |
| 2017/0340434 A1* | 11/2017 | Cerchiari | A61B 17/12118 |
| 2019/0021844 A1* | 1/2019 | Palmaz | A61F 2/07 |

FOREIGN PATENT DOCUMENTS

| | | |
|---|---|---|
| JP | 2007-526039 A | 9/2007 |
| JP | 5070373 B2 | 11/2012 |
| JP | 2014-526929 A | 10/2014 |
| JP | 2015-527156 A | 9/2015 |
| WO | 03/28522 A2 | 4/2003 |

* cited by examiner

TOTAL ARCH CONCEPT

CROSS-REFERENCE TO RELATED APPLICATION

This application claims priority to Provisional Application No. 62/385,484, filed Sep. 9, 2016, entitled, TOTAL ARCH CONCEPT, which is herein incorporated by reference in its entirety.

TECHNICAL FIELD

The present invention relates to medical devices and methods for treating an anatomical space of the body. More specifically, the invention relates to methods, apparatuses, and systems that include a prosthesis that allows for accurate deployment to treat dissections and aneurysms in the said anatomical space.

BACKGROUND

Disease of the vasculature is increasingly common. Treatment of the vasculature may be difficult to provide proper treatment because of the tortuous nature and complexity of the vasculature. Aortic dissections, for example, commonly begin at or near the aortic valve root and continue to the ascending aorta and the aortic arch, and may also affect the upper part of the descending aorta. Medical devices implanted at a diseased state may be used for treatment of aortic dissections, aneurysms, and other diseases of the vasculature.

It remains desirable to provide medical devices, systems and methods for repairing disease along the aorta and also for repairing disease along the aorta and the branches extending therefrom.

SUMMARY

Various aspects of the present disclosure are directed toward devices, systems and methods that include a prosthesis that may include a first graft component and a second graft component. The second graft component may be arranged within the first graft component and coupled thereto. Further, the second graft component may have a dog bone shape, hour glass shape, or other shape that includes an intermediate portion having a diameter that is less that a diameter of one or more of end portions of the second graft component. The prosthesis may also include a gap arranged between the first graft component and the second graft component. In addition, the prosthesis may include a stent structure arranged with the first graft component.

Aspects of the present disclosure are also directed toward devices, systems and methods that include a prosthesis having a first graft component, a second graft component arranged within the first graft component, and a stent structure arranged with the first graft component. The second graft component may include a first end portion, a second end portion, and an intermediate portion with the intermediate portion having a diameter less than a diameter of at least one of the first end portion and the second end portion. The prosthesis may also include a portal bridge arranged between a first opening in the first graft component and a second opening in the second graft component. Further, the prosthesis may include a gap arranged between the first graft component and the second graft component.

Various aspects of the present disclosure may also be directed toward devices, systems and methods that include a prosthesis having a first graft component and a second graft component arranged within the first graft component and coupled thereto at end portions of the second graft component and end portions of the first graft component. The prosthesis may include a space formed by the first graft component and the second graft component and arranged between the end portions of the first graft component and the end portions of the second component. The prosthesis may also include a stent structure arranged with the first graft component.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
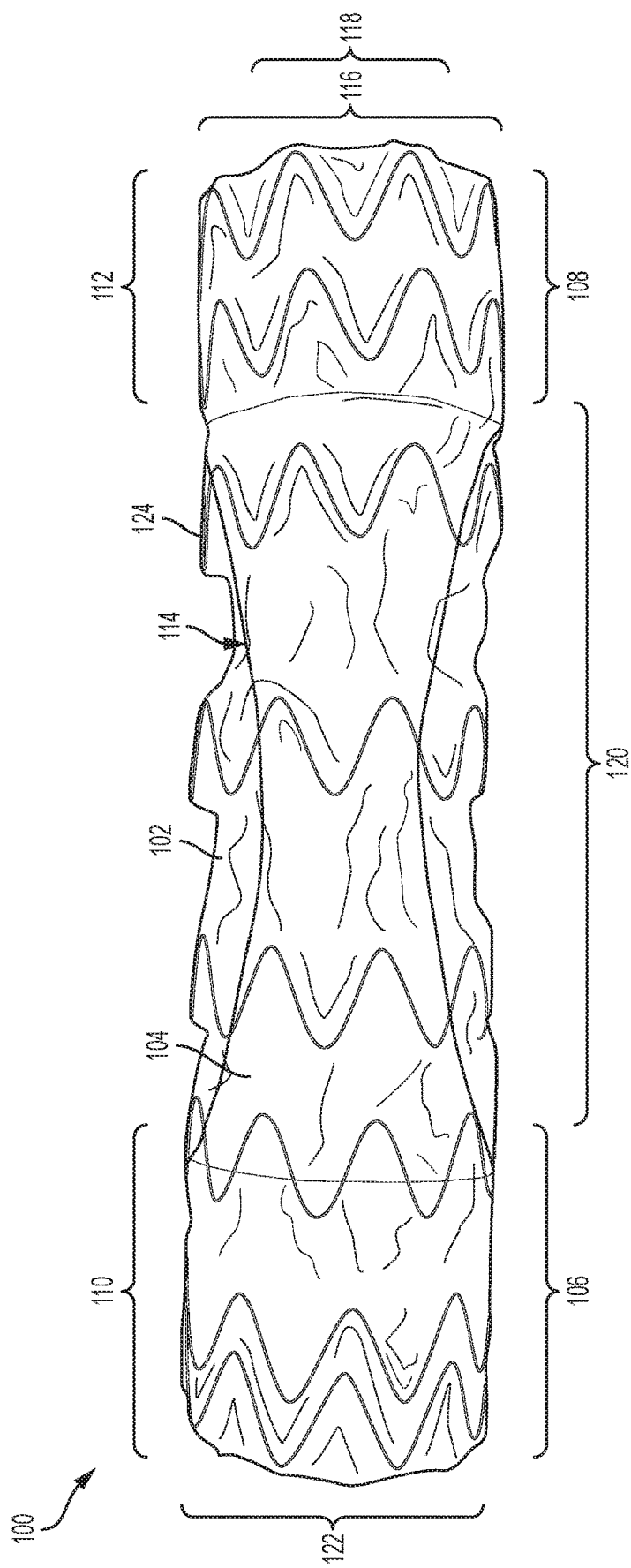
FIG. 1 is an illustration of an example prosthesis device consistent with various aspects of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various aspects of the present disclosure are directed toward apparatuses, systems, and methods that include a prosthesis device that may be used in treatment of the vasculature. As described in further detail below, the prosthesis device may be configured to conform to the vasculature into which the prosthesis is implanted. In addition, the prosthesis device may be low profile in order to enable delivery thereof using a minimally invasive procedure (e.g., transcatheter). Further, the prosthesis device may be sufficiently durable to withstand forces and other stresses that occur once implanted in the vasculature.

FIG. 1 is an illustration of an example prosthesis device 100 consistent with various aspects of the present disclosure. The prosthesis device 100 may include a first graft component 102 and a second graft component 104. The second graft component 104 is arranged within the first graft component 102 and coupled thereto at end portions 106, 108 of the second graft component 104 and end portions 110, 112 of the first graft component 102. The end portions 106, 108 of the second graft component 104 and the end portions 110, 112 of the first graft component 102 may be attached to one another using an adhesive between the first graft component 102 and the second graft component 104, bonding the first graft component 102 to the second graft component 104, heat bonding the first graft component 102 to the second graft component 104 (e.g., with fluorinated ethylene propylene (FEP) between the layers), or any combination thereof. The end portions 106, 108 of the second graft component 104 and the end portions 110, 112 of the first graft component 102 may be coupled to one another around the entire circumference of the first graft component 102 and the second graft component 104. In certain instances, attaching the first graft component 102 to the second graft component 104 in this manner may prevent air or other fluids (e.g., blood) from entering between the first graft component 102 the second graft component 104.

The prosthesis 100 may also include a space 114 formed by (and between) the first graft component 102 and the second graft component 104. The space 114 may be arranged between the end portions 106, 108 of the second graft component 104 and the end portions 110, 112 of the first graft component 102. The space 114 formed by and between the first graft component 102 and the second graft component 104 may be an opening, void, or unoccupied area that is formed based on the first graft component 102 and the second graft component 104 being physically separated from one another. In addition, the first graft component 102 and the second graft component 104 may maintain the space 114 in response to forces applied to one or more of the first graft component 102 and the second graft component 104. The space 114 may be configured such that at least certain portions of the first graft component 102 remain uncoupled to and uncontacted with the second graft component 104.

In certain instances, the space 114 and the separation between the first graft component 102 and the second graft component 104 may be formed by portions of and the second graft component 104 having a different diameter than the first graft component 102. In certain instances, the first graft component 102 may have a first diameter 116, and at least a portion of the second graft component 104 includes a second diameter 118, with the second diameter 118 being less than the first diameter 116. The first diameter 116 may be a constant diameter across a length of the prosthesis 100. In certain instances, the second graft component 104 may include an intermediate portion 120 arranged between the end portions 106, 108. The intermediate portion 120 is of the second diameter 118, which is less than the first diameter 116.

The end portions 106, 108 of the second graft component 104 may include a third diameter 122. The third diameter 122 may be greater than the second diameter 118. In certain instances, the third diameter 122 may be slightly less than or equal to the first diameter 116. More specifically, the second graft component 104, with the end portions 106, 108 being of the third diameter 122, is arranged within the first graft component 102, being of the first diameter 116. Thus, the third diameter 122 is less than the first diameter 116 when the second graft component 104 is arranged within the first graft component 102. However, the third diameter 122 may be equal to the first diameter 116 prior to arranging the second graft component 104 within the first graft component 102.

In addition, one or more of the end portions 106, 108 of the second graft component 104 may taper toward the intermediate portion 120 of the second graft component 104. As a result, one or more of the end portions 106, 108 of the second graft component 104 may have an intermediate or transition diameter in transition from the third diameter 122 to the second diameter 118. The taper from the third diameter 122 to the second diameter 118 may be a constant linear taper, the taper may vary, or the taper may follow an exponential decrease. In certain instances, each of the end portions 106, 108 of the second graft component 104 taper toward the intermediate portion 120 of the second graft component 104. The second graft component 104 may also form a shape that may include a dog bone shape or an hourglass shape. In certain instances, the second diameter 118 may be between 10% and 30% of the first diameter 116. The difference between the first diameter 116 and the second diameter 118 may mitigate against kinking of the second graft component 104 when the prosthesis device 100 is deployed within a vessel such as the aorta.

Lengths of one or more of the end portions 106, 108 and the intermediate portion 120 of the second graft component 104 may vary. More specifically, the lengths of one or more of the end portions 106, 108 may each comprise 5%, 10%, 15%, 20%, 25%, 30% or any percentage therebetween a length of the prosthesis 100 greater. The lengths of the end portions 106, 108 may be equal to one another or the lengths of the end portions 106, 108 may differ from one another.

The prosthesis may also include a stent structure 124. The stent structure 124 may be arranged on the first graft component 102. In certain instances, the stent structure 124 may be attached to an exterior surface of the first graft component 102. In addition, the space 114 formed by the first graft component 102 and the second graft component 104 may mitigate against the stent structure 124 contacting at least a portion of the second graft component 104. More specifically, the space 114 may be configured such that the stent structure 124 does not contact the intermediate portion 120 of the second graft component 104. The stent structure 124 may be formed by discrete stent rings, or a continuous sinusoidal pattern.

Figure 2:
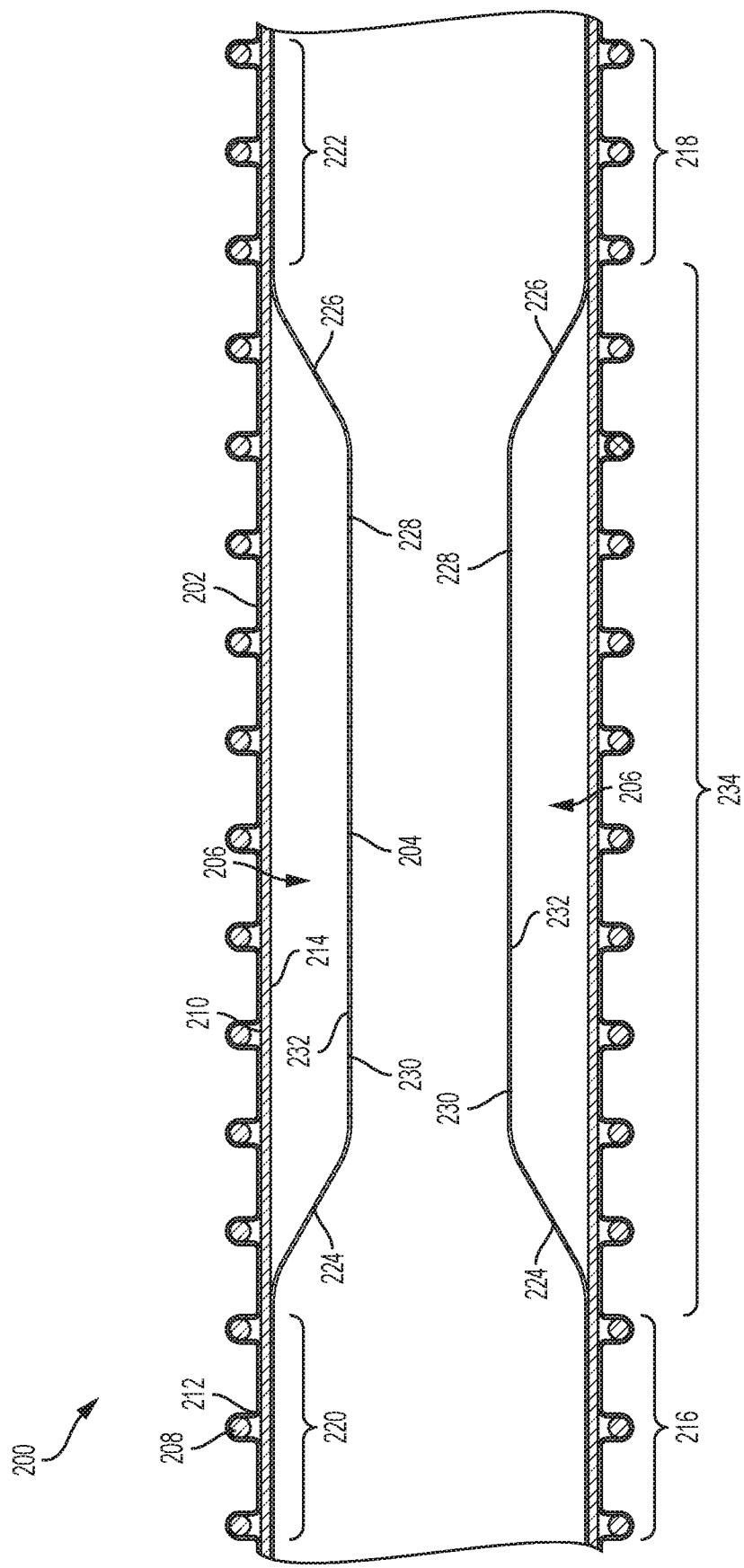
FIG. 2 is cross-sectional view of an example prosthesis device consistent with various aspects of the present disclosure.

FIG. 2 is cross-sectional view of an example prosthesis device 200 consistent with various aspects of the present disclosure. The prosthesis device 200 may include a first graft component 202 and second graft component 204 arranged within the first graft component 202 and coupled thereto. As shown in FIG. 2, the second graft component 204 may include a dog bone or hourglass shape (or other shape that includes an intermediate portion having a diameter than is less that a diameter of one or more of end portions). As a result of the shape of the second graft component 204, the prosthesis 200 may include a gap 206 arranged between the first graft component 202 and the second graft component 204. The gap 206 is arranged around a circumference of the prosthesis device 200 between the first graft component 202 and the second graft component 204. In addition, the gap 206 may be formed based on manner in which the first graft component 202 is coupled to the second graft component 204.

As discussed in further detail below, portions of the first graft component 202 may be permanently coupled to the second graft component 204. The first graft component 202 and the second graft component 204 may be attached using an adhesive between portions of the first graft component 202 and the second graft component 204, bonding portions of the first graft component 202 to the second graft component 204, heat bonding portions of the first graft component 202 to the second graft component 204 or any combination thereof. Coupling the first graft component 202 and the second graft component 204 in this manner forms a cohesive, interconnected, and complete graft component combination. As a result, forces or pressures acting on one of the first graft component 202 and the second graft component 204 may be transferred to the other of the first graft component 202 and the second graft component 204. In addition, the first graft component 202 and the second graft component 204 may expand from a delivery configuration to an expanded configuration, show in FIG. 2, as a unit. The delivery configuration of the prosthesis 200 is discussed in further detail below with reference to FIG. 5A.

The prosthesis 200 also may include a stent structure 208 arranged with the first graft component 202. As shown in FIG. 2, the stent structure 208 may be formed by discrete stent ring structures arranged about the circumference of the first graft component 202. The stent structure 208 may be arranged on an exterior surface 210 of the first graft component 202. The stent structure 208 may be attached to the exterior surface 210 by an attach tape 212. The attach tape 212 may be formed of a similar material as the first graft component 202 and the second graft component 204. The attach tape 212 may include a layer of adhesive (e.g., FEP) that is used to attach portions of the attach tape 212 to the exterior surface 210 of the first graft component 202 and secure the stent structure 208 to the first graft component 202. The attach tape 212 may be biased to one side of each of the stent structure 208. The stent structure 208 may include a plurality of apices. The attach tape 212 may be biased to one side of each of the apices, which may enhance the flexibility of the prosthesis 200. In certain instances, a leading or peak of each of the apices is uncovered by the attach tape 212.

Portions of an interior surface 214 of the first graft component 202 may be the portion of the first graft component 202 that attach to the second graft component 204. More specifically, end portions 216, 218 of the first graft component 202 and thus end portions of the interior surface 214 may be attached to end portions 220, 222 of the second graft component 204. To form the dog bone or hourglass shape, the second graft component 204 may also include tapered portions 224, 226 and an intermediate portion 228. The tapered portions 224, 226 decrease a diameter of the second graft component 204 form the end portions 220, 222 to the intermediate portion 228. The tapered portions 224, 226 may provide a linear and constant decrease in the diameter of the second graft component 204. The tapered portions 224, 226 may also provide a varied decrease in diameter of the second graft component 204, or the decrease may be exponential.

In certain instances, the first graft component 202 is configured to stretch in response to a force applied to any portion (at least one of the first graft component 202, the second graft component 204, and the stent structure 208) of the prosthesis 200. The second graft component 204 is configured to substantially maintain the dog bone or the hour glass shape in response to the forces applied to the prosthesis 200. In addition, the first graft component 202 may be configured to maintain the gap 206 between the first graft component 202 and the second graft component 204 in response to the force applied to the prosthesis 200. As a result, the first graft component 202 mitigates against the stent structure 208 contacting the second graft component 204. While the prosthesis 200 is implanted, forces (e.g., tensile, radial, extension) imparted on the first graft component 202, the second graft component 204, or the stent structure 208 may structurally stress the components of the prosthesis 200. The stent structure 208 may be formed of a metal or similar material. Thus, the first graft component 202 may be configured to mitigate against the stent structure 208 rubbing or puncturing the first graft component 202 or the second graft component 204, which may compromise the effectiveness of the prosthesis 200. The forces may be stretching or tensile forces that result from implanting the prosthesis 200 in the vasculature, movement of the patient into which the prosthesis 200 is implanted, forces external from the vasculature, and/or forces internal to the vasculature.

The first graft component 202 may also be configured to stretch in response to a pressure that originates from at least one of: within the second graft component 204, between the first graft component 202 and the second graft component 204 (e.g., within the gap 206), and external to the first graft component 202. The second graft component 204 includes an interior surface 230 and an exterior surface 232. The second graft component 204 of the interior surface 230 may be configured to form a blood flow lumen, and the exterior surface 210 of the first graft component 202 may be configured to contact a vessel wall. Thus, the pressure within the second graft component 204 may be due to blood flow through the prosthesis 200, and pressure external to the first graft component 202 may be the result of the vessel wall.

In certain instances, the first graft component 202, the second graft component 204, and the stent structure 208 are configured to conform to a shape of a vessel wall. The first graft component 202 is configured to stretch and maintain the gap 206 between the first graft component 202 and the second graft component 204 in response conforming to the shape of the vessel wall. The stretch of the first graft component 202 may enhance the ability of the prosthesis 200 to conform to the vessel wall within the vasculature.

As noted above, the end portions 216, 218 of the first graft component 202 may be attached to the end portions 220, 222 of the second graft component 204. The first graft component 202 also includes an intermediate portion 234 that is not attached to the second graft component 204. The intermediate portion 234 of the first graft component 202 is arranged between the end portions 216, 218 of the first graft component 202 and may be configured to move independently of the second graft component 204.

In certain instances, the first graft component 202 includes a first mass per area and a first tensile strength, the second graft component 204 includes a second mass per area and a second tensile strength. The first mass per area may be less than the second mass per area, and/or the first tensile strength may be less than the second tensile strength. In certain instances, the first mass per area may be less than the second mass per area, and the first tensile strength may be less than the second tensile strength.

The illustrative prosthesis 200 shown in FIG. 2 is not intended to suggest any limitation as to the scope of use or functionality of embodiments of the disclosure disclosed throughout this document. Neither should the illustrative prosthesis 200 be interpreted as having any dependency or requirement related to any single component or combination of components illustrated therein. For example, in embodiments, the illustrative prosthesis 200 may include additional components such as, for example, a portal bridge as described in further detail with reference to FIG. 3 and FIG. 4. Additionally, any one or more of the components depicted in FIG. 2 can be, in embodiments, integrated with various ones of the other components depicted therein (and/or components not illustrated). More specifically, the first graft component 102 may be configured to stretch, include a tensile strength and/or mass per area as described with reference to the first graft component 202, and the second graft component 104 may include a tensile strength and/or mass per area as described with reference to the second graft component 204.

Figure 3:
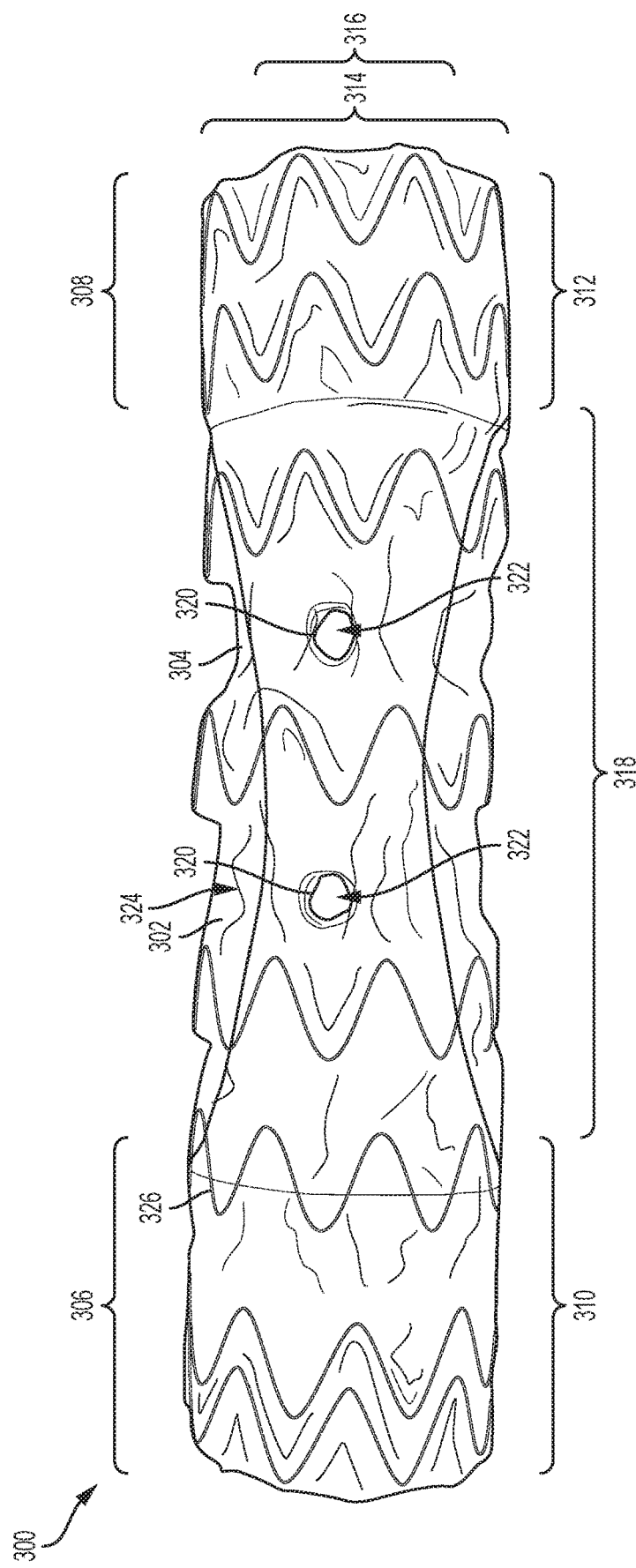
FIG. 3 is a side view of an example prosthesis device consistent with various aspects of the present disclosure.

FIG. 3 is a side view of an example prosthesis device 300 consistent with various aspects of the present disclosure. The prosthesis device 300 may include a first graft component 302 and a second graft component 304. The second graft component 304 is arranged within the first graft component 302 and coupled thereto at end portions 306, 308 of the first graft component 302 and end portions 310, 312 of the second graft component 304. The end portions 306, 308 of the first graft component 302 and end portions 310, 312 of the second graft component 304 may be attached to one another using an adhesive between the first graft component 302 and the second graft component 304. One or more of the end portions 306, 308 of the first graft component 302 and may have an equal length to a corresponding one of the end portions 310, 312 of the second graft component 304. In addition, the end portions 306, 308 and the end portions 310, 312 may be coupled to one another around the entire circumference of the prosthesis 300. In certain instances, attaching the first graft component 302 to the second graft component 304 in this manner may prevent air or other fluids (e.g., blood) from entering between the first graft component 302 the second graft component 304. In addition, attaching the first graft component 302 to the second graft component 304 in this manner may form unitary graft structure.

As shown in FIG. 3, the first graft component 302 may include a first diameter 314 that is approximately constant through a length of the first graft component 302. The second graft component 304 may include portions that have a second diameter 316 that is less than the first diameter 314. The second graft component 304 may include an intermediate portion 318 arranged between the end portions 310, 312. The intermediate portion 318 is of the second diameter 316. In certain instances, the end portions 306, 308 of the first graft component 302 and end portions 310, 312 of the second graft component 304 may have the same first diameter 314. The end portions 310, 312 and the intermediate portion 318 of the second graft component 304 may form an hourglass or dogbone shape. In certain instances, the second diameter 316 may be between 10% and 30% of the first diameter 314. The difference between the first diameter 314 and the second diameter 316 may mitigate against kinking of the second graft component 304 when the prosthesis device 300 is deployed within a vessel such as the aorta.

The prosthesis 300 may also include one or more portal bridges 320. As shown in FIG. 3, the prosthesis 300 may include two portal bridges 320. The portal bridges 320 may include openings 322 that are configured to provide a fluid conduit from the second graft component 304. The prosthesis 300 is configured for placement within a vessel. The portal bridges 320 may also be configured to accept a side branch device therethrough and facilitate placement of the branched device within a side branch vessel (adjacent to the vessel in which the prosthesis 300 is implanted). Further detail regarding the portal bridges 320 is discussed in connection with FIG. 4.

The prosthesis 300 may also include a space or gap 324 formed by (and between) the first graft component 302 and the second graft component 304. The space or gap 324 may be arranged between the end portions 306, 308 of the first graft component 302 and end portions 310, 312 of the second graft component 304. The gap 324 formed by and between the first graft component 302 and the second graft component 304 may be an opening, void, or unoccupied area that is formed based on the first graft component 302 and the second graft component 304 being physically separated from one another. In addition, the first graft component 302 and the second graft component 304 may maintain the gap 324 in response to forces applied to any portion of the prosthesis 300. The gap 324 may be configured such that at least certain portions of the first graft component 302 remain uncoupled to and uncontacted with certain portions of the second graft component 304. The gap 324 may be formed about the entire circumference of the prosthesis 300.

The prosthesis may also include a stent structure 326. The stent structure 326 may be arranged on and attached to the first graft component 302. In addition, the gap 324 formed by the first graft component 302 and the second graft component 304 may mitigate against the stent structure 326 contacting at least a portion of the second graft component 304. More specifically, the gap 324 may be configured such that the stent structure 326 does not contact the intermediate portion 318 of the second graft component 304. The stent structure 326 may be formed by discrete stent rings, each of which include a sinusoidal pattern.

In certain instances, the first graft component 302 includes a first mass per area and a first tensile strength, the second graft component 304 includes a second mass per area and a second tensile strength. The first mass per area may be less than the second mass per area, and/or the first tensile strength may be less than the second tensile strength. In certain instances, the first mass per area may be less than the second mass per area, and the first tensile strength may be less than the second tensile strength. As a result, the first graft component 302 may be configured to stretch in response to a force applied to any portion of the prosthesis 300. The first graft component 302 being configured to stretch assists in maintaining the gap 324 between the first graft component 302 and the second graft component 304 in response to the force applied to the prosthesis 300. Stretching may enhance the ability of the prosthesis 300 to conform to the vessel into which the prosthesis 300 is implanted. In addition, the first graft component 302 may be configured to mitigate against the stent structure 326 rubbing or puncturing the first graft component 302 or the second graft component 304, which may compromise the effectiveness of the prosthesis 300, by stretching and maintaining the gap 324.

Figure 4:
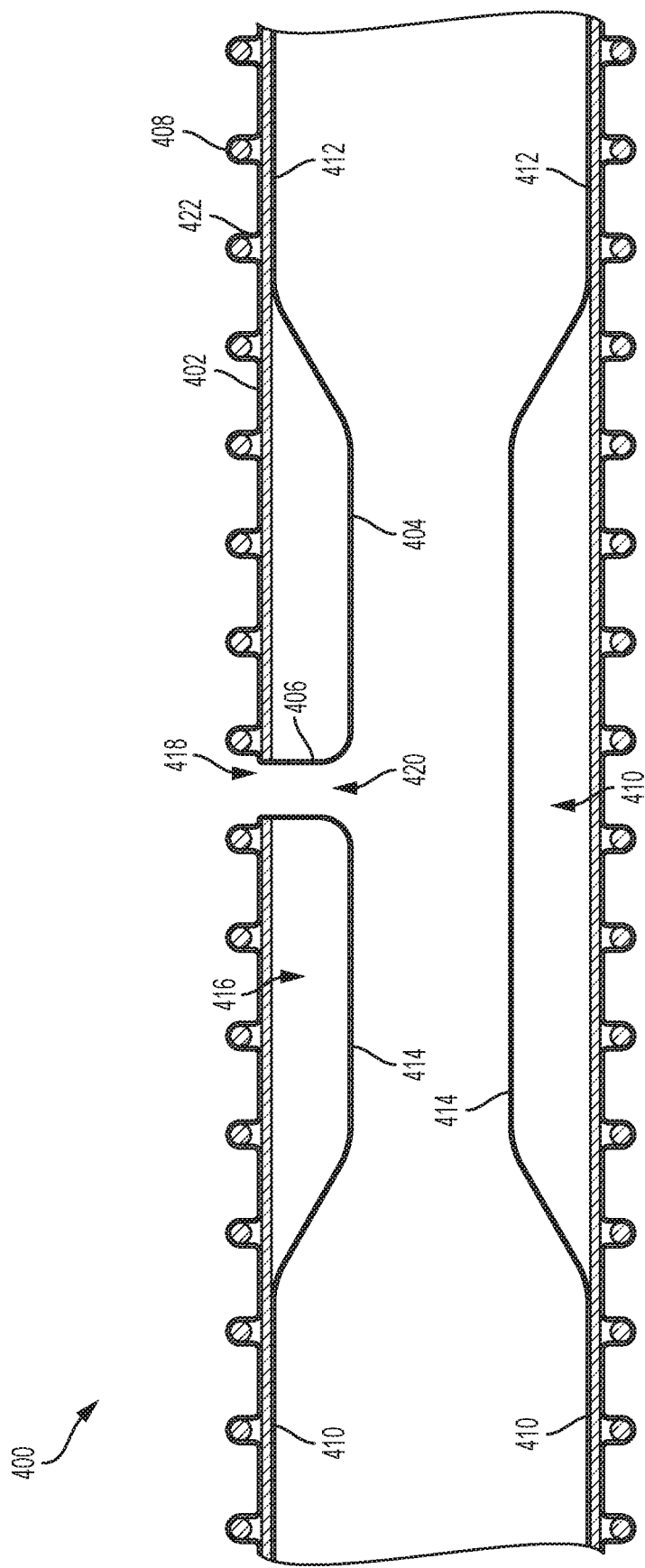
FIG. 4 is cross-sectional view of an example prosthesis device having a portal bridge consistent with various aspects of the present disclosure.

FIG. 4 is cross-sectional view of an example prosthesis device 400 having a portal bridge 406 consistent with various aspects of the present disclosure. Although a single portal bridge 406 is shown in FIG. 4, the prosthesis device 400 may include one, two, three, four, or any number of portal bridges 406. In addition, the portal bridges 406 may be arranged along any side of the prosthesis 400. Thus, the prosthesis 400 may include a portal bridge 406 facing one direction, another portal bridge 406 facing the same direction, another portal bridge 406 facing the opposite direction, or combinations thereof with additional portal bridges 406.

The prosthesis 400 may also include a first graft component 402, a second graft component 404, and a stent structure 408. The stent structure 408 may be attached to the first graft component 402 using an attach tape 422 may be formed of a similar material as the first graft component 402 and the second graft component 404. The attach tape 422 may include a layer of adhesive (e.g., FEP) that is used to attach portions of the attach tape 422 to the first graft component 402 and secure the stent structure 408 to the first graft component 402. The attach tape 422 may be biased to one side of each of the stent structure 408. As shown in FIG. 1, the stent structure 124 may include a plurality of apices.

The attach tape 422 may be biased to one side of each of the apices, which may enhance the flexibility of the prosthesis 400. In certain instances, a leading or peak of each of the apices is uncovered by the attach tape 422, which may be helically wound around the prosthesis 400.

The second graft component 404 is arranged within the first graft component 402 and coupled thereto. The second graft component 404 may include a first end portion 410, a second end portion 412, and an intermediate portion 414. The first end portion 410 and the second end portion 412 of the second graft component 404 may be attached to the first graft component 402 to couple the first graft component 402 to the second graft component 404. As a result, forces or pressures acting on one of the first graft component 402 and the second graft component 404 may be transferred to the other of the first graft component 402 and the second graft component 404. In addition, the first graft component 402 and the second graft component 404 may expand together as a unitary structure (along with the stent structure 408). In addition, the intermediate portion 414 includes a diameter that is less than a diameter of at least one of the first end portion 410 and the second end portion 412. As shown in FIG. 4, the intermediate portion 414 includes a diameter that is less than a diameter of each of the first end portion 410 and the second end portion 412. A diameter of the first graft component 402 may be equal to or substantially equal to (within 1%) of the diameter of the first end portion 410 and the second end portion 412.

As a result of the second graft component 404 having portions of different diameters, a gap 416 is arranged between the first graft component 402 and the second graft component 404. The gap 416 may be arranged about the circumference of the prosthesis 400, and may be arranged between the first end portion 410 and the second end portion 412 of the second graft component 404. In certain instances, the first graft component 402 is configured to stretch in response to a force applied to any portion (at least one of the first graft component 402, the second graft component 404, and the stent structure 408) of the prosthesis 400. The first graft component 402 may be configured to maintain the gap 416 between the first graft component 402 and the second graft component 404 in response to the force applied to the prosthesis 400. As a result, the first graft component 402 mitigates against the stent structure 408 contacting the second graft component 404.

While the prosthesis 400 is implanted, forces (e.g., tensile, radial, extension) or pressures imparted on the first graft component 402, the second graft component 404, or the stent structure 408 may structurally stress the components of the prosthesis 400. Thus, the first graft component 402 may be configured to mitigate against the stent structure 408 rubbing or puncturing the first graft component 402 or the second graft component 404, which may compromise the effectiveness of the prosthesis 400. The forces may be stretching or tensile forces that result from implanting the prosthesis 400 in the vasculature, movement of the patient into which the prosthesis 400 is implanted, forces external from the vasculature, and/or forces internal to the vasculature. The ability of the first graft component 402 to stretch may also enhance the ability of the prosthesis 400 to conform to the vasculature. The first graft component 402 being configured to stretch enhances the ability of the prosthesis 400 to react to bending.

Figure 5A:
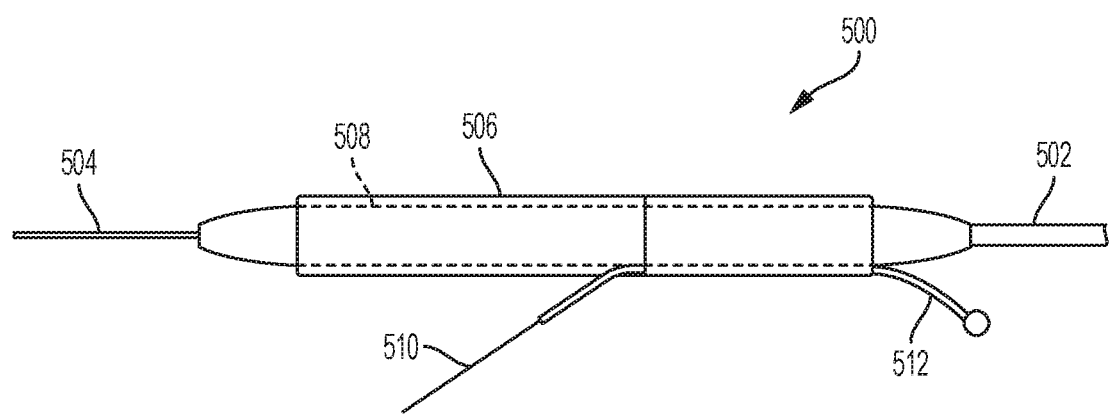
FIG. 5A illustrates a step in deploying an example prosthesis device consistent with various aspects of the present disclosure.

As noted above, the portal bridge 406 may connect the first graft component 402 and the second graft component 404. The first graft component 402 includes a first opening 418 and the second graft component 404 includes a second opening 420. The portal bridge 406 is formed between the first opening 418 and the second opening 420. The portal bridge 406 may be formed of a graft structure or component. In certain instances, the portal bridge 406 may be formed of a portion of the second graft component 404. The second graft component 404 may include a smooth inner flow surface along a length thereof, including up into a smooth transition to an interior surface of the portal bridge 406 as a result of being formed in this manner. In addition, the portal bridge 406 may be free of any stent or other support components. In deploying the prosthesis 400, the portal bridge 406 may self-deploy. The prosthesis 400 is collapsed in a delivery configuration (as shown in FIG. 5A) such that a circumference of the prosthesis 400 in the delivery configuration is less than a circumference of the prosthesis 400 in a deployed configuration. FIG. 4 shows the prosthesis 400 in the deployed configuration. The portal bridge 406 is attached to the first opening 418, and may be formed of a portion of the second graft component 404. Thus, in expanding of the prosthesis 400 from the delivery configuration to the deployed configuration, the portal bridge 406 is pulled open by separation of the first graft component 402 and the second graft component 404.

Once implanted, an external surface of the first graft component 402 and the stent structure 408 may be configured to contact a vessel wall, and an interior surface of the second graft component 404 may be configured as a blood flow lumen. Blood may also flow through the portal bridge 406, which may be arranged adjacent to a side branch of the vessel that the prosthesis 400 is deployed within. More specifically, the prosthesis 400 may be deployed within the aorta, and the portal bridge 406 may be arranged adjacent to one of the three branch vessels off the aortic arch (e.g., the brachiocephalic (innominate) artery, common carotid arteries, subclavian arteries)

Figure 5B:
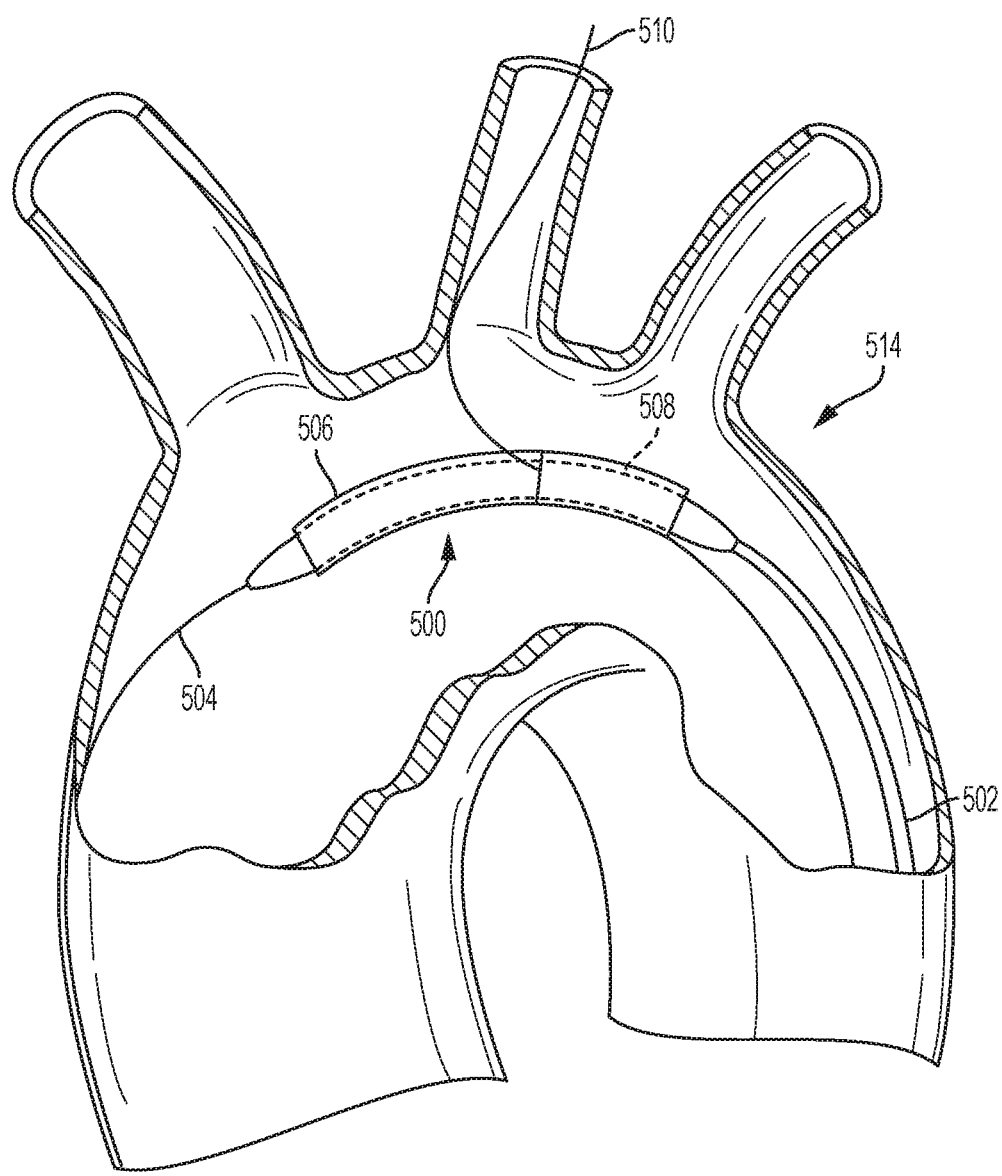
FIG. 5B illustrates another step in deploying the example prosthesis device shown in FIG. 5A consistent with various aspects of the present disclosure.
Figure 5C:
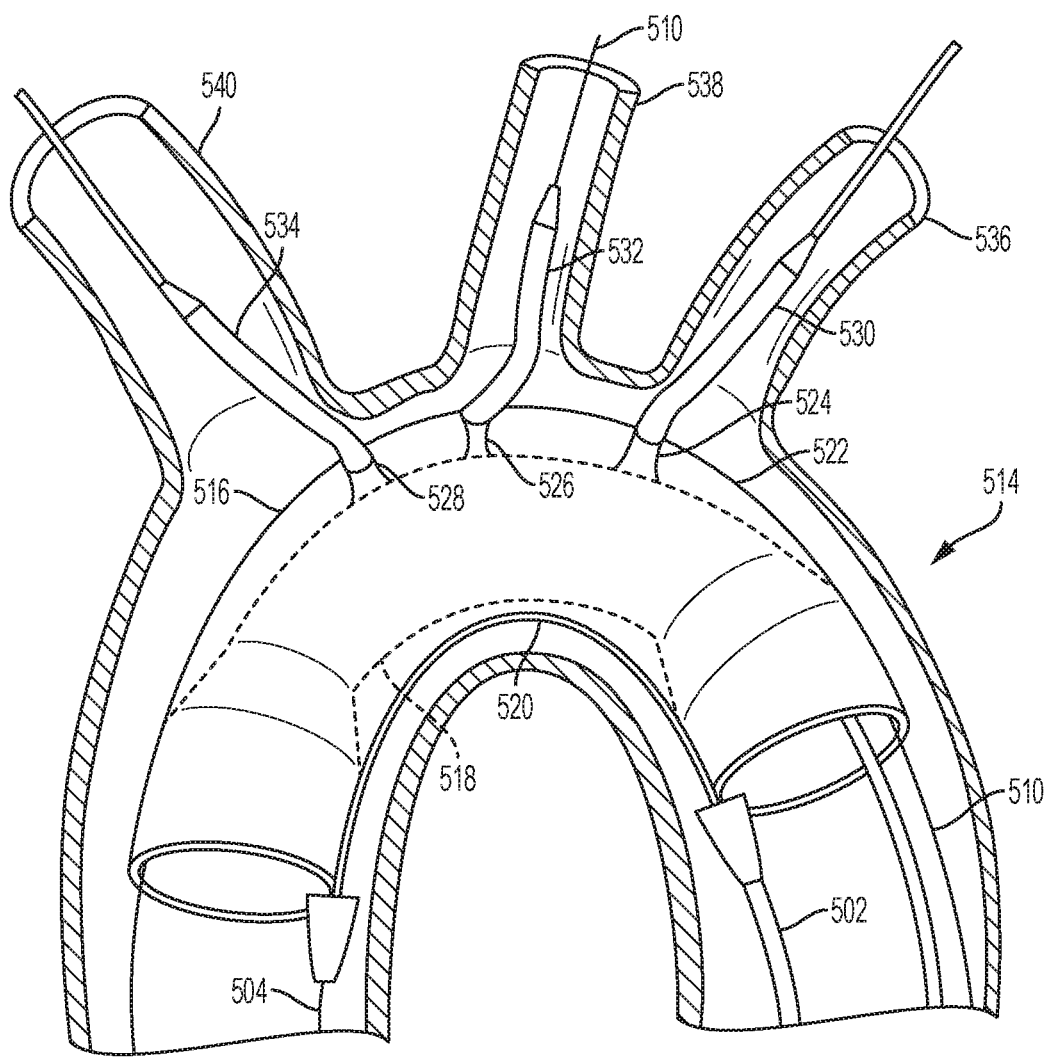
FIG. 5C illustrates another step in deploying the example prosthesis shown in FIGS. 5A-B consistent with various aspects of the present disclosure.

As shown in further detail with reference to FIG. 5C, the portal bridge 406 is configured to accept a side branch device therethrough and facilitate placement of the branched device within a side branch vessel. The portal bridge 406 is configured to self-deploy and open to accept the side branch device therethrough and facilitate placement of the branched device within the side branch vessel.

FIG. 5A illustrates a step in deploying an example prosthesis device 500 consistent with various aspects of the present disclosure. The example prosthesis device 500 may be one of prosthesis device 100, prosthesis device 200, prosthesis device 300, or prosthesis device 400 discussed above. Each of these devices may be low-profile along with conformable and durable as discussed above. As shown in FIG. 5A, the prosthesis device 500 is collapsed on a delivery system 502. The outer diameter of the delivery system 502 may be less than 22 French.

As shown in FIG. 5A, the delivery system 502 includes a main guidewire 504 that may be used to route the delivery system 502 to a target location within the vasculature. The delivery system 502, for example, may be routed through a patient's femoral artery. The prosthesis 500 may be provided in a constrained state by a flexible primary sleeve 506 on a distal end of the delivery system 502. An optional flexible secondary sleeve 508 may be provided and disposed around the prosthesis 500 to constrain the prosthesis 500 in a partially deployed state after opening the primary sleeve 506 to facilitate positioning of the device at the treatment prior to final deployment. Further detail of the sleeves, construction and deployment are provided in U.S. Pat. No. 5,919,225 to Lau et al., and U.S. Publication 2010/0049294 to Zukowski et al., the entire contents of which are incorporated herein by reference for all purposes.

In a certain instances, the prosthesis 500 may include one or more portal bridges. In order to align the portal bridge within the vasculature, a branch guidewire 510 may be used to align the portal bridge with an intended side branch vessel. A guidewire tube or conduit 512 for each branch member to be deployed is positioned through the prosthesis 500 may be used to load the branch guidewire 510 through the prosthesis 500 as constrained by the primary sleeve 506. The guidewire tube or conduit 512 preserves a lumen through which the branch guidewire 510 can be inserted while the prosthesis 500 remains constrained by the primary sleeve 506. The guidewire tube or conduit 512 is removed prior to implantation of the prosthesis 500. Further detail of the conduit, construction and deployment are provided in U.S. Patent Publication 2008/0269866 to Hamer et al., the entire content of which is incorporated herein by reference for all purposes.

As illustrated in FIG. 5B, the constrained prosthesis 500 is advanced within the vasculature to a target location 514 via the femoral artery. The target location 514 may be the aortic arch of the patient. The respective main 504 and branch guidewire 510 are directed toward the target location 514. Thus the main guidewire 504 is routed to the aortic arch, and the branch guidewire 510 is routed to one of the branch vessels.

The prosthesis 500 is shown in a deployed configuration in FIG. 5C. As shown therein, the prosthesis 500 includes a first graft component 516 and a second graft component 518. The prosthesis 500 may also include a stent structure (as discussed above). The prosthesis 500 includes an inner curvature 520 and an outer curvature 522. As discussed in detail above, the first graft component 516 is configured to stretch to enhance the ability of the prosthesis 500 to conform to the target location 514 and take the shape of the inner curvature 520 and the outer curvature 522.

The prosthesis 500 includes three portal bridges 524, 526, 528 arranged between openings in the first graft component 516 and the second graft component 518. Each of the portal bridges 524, 526, 528 are configured to self-deploy and open to accept side branch devices 530, 532, 534 therethrough and facilitate placement of the side branch devices 530, 532, 534 within the side branch vessels 536, 538, 540. Each of the side branch devices 530, 532, 534 are routed using respective branch guide wires as described above with reference to branch guidewire 510. In addition, the side branch devices 530, 532, 534 are arranged in a constrained state on a distal end of a branch catheters utilizing a branch constraining sleeve, as described above for the prosthesis 500. The side branch devices 530, 532, 534 are then advanced and positioned through a respective one of the portal bridges 524, 526, 528, and into one of the side branch vessels 536, 538, 540 along the aortic arch. The side branch devices 530, 532, 534 may be deployed in the side branch vessels 536, 538, 540.

The illustrative components shown in FIGS. 1-5 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the prostheses depicted in any of the FIGS. 1-5 may be, in embodiments, integrated with various other components depicted therein (and/or components not illustrated), all of which are considered to be within the ambit of the disclosed subject matter.

The prostheses discussed herein may include a number of graft components. The graft components may be formed from but are not limited to nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a graft material. In one embodiment, the graft is made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. In another embodiment, the graft comprises expanded fluorocarbon polymers (especially PTFE) materials. Included in the class of preferred fluoropolymers are polytetrafluoroethylene (PTFE), fluorinated ethylene propylene (FEP), copolymers of tetrafluoroethylene (TFE) and perfluoro (propyl vinyl ether) (PFA), homopolymers of polychlorotrifluoroethylene (PCTFE), and its copolymers with TFE, ethylenechlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is ePTFE. In another embodiment, the graft comprises a combination of the materials listed above. In another embodiment, the graft is substantially impermeable to bodily fluids. The substantially impermeable graft can be made from materials that are substantially impermeable to bodily fluids or can be constructed from permeable materials treated or manufactured to be substantially impermeable to bodily fluids (e.g. by layering different types of materials described above or known in the art). In one embodiment, the main body and branch members, as described above, are made from any combinations of the materials above. In another embodiment, the main body and branch members, as described above, comprise ePTFE. Further, in a variety of embodiments, a graft can comprise expanded fluorocarbon polymers (especially PTFE), materials described in U.S. Pat. Nos. 3,953,566; 4,187,390; or 5,276,276, which are herein incorporated by reference for their teachings in their entireties.

The stents, as described above, may be generally cylindrical when restrained and/or when unrestrained and comprise helically arranged undulations having plurality of helical turns. The undulations preferably are aligned so that they are "in-phase" with each other. More specifically, undulations comprise apices in opposing first and second directions. When the undulations are in-phase, apices in adjacent helical turns are aligned so that apices can be displaced into respective apices of a corresponding undulation in an adjacent helical turn. In one embodiment, the undulations have a sinusoidal shape. In another embodiment, the undulations are U shaped. In another embodiment, the undulations are V shaped. In another embodiment, the undulations are ovaloid shaped. These shapes are fully described in U.S. Pat. No. 6,042,605. U.S. Pat. No. 6,042,605 is incorporated by reference herein in its entirety for all purposes. The stents described herein may be formed from a variety of materials variously metallic, super elastic alloys, such as Nitinol. Various stainless steels which have been physically, chemically, and otherwise treated to produce high springiness are suitable as are other metal alloys such as cobalt chrome alloys, platinum/tungsten alloys, and especially the nickel-titanium alloys generically known as "nitinol".

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

I claim:

1. A prosthesis comprising:
a first graft component including a first mass per area and a first tensile strength;
a second graft component arranged within the first graft component and coupled thereto, the second graft component having a dog bone shape and including a second mass per area and a second tensile strength, and at least one of the first mass per area and the first tensile strength differs from at least one of the second mass per area and the second tensile strength;
a gap arranged between the first graft component and the second graft component; and
a stent structure arranged with the first graft component.

2. The prosthesis of claim 1, wherein the first graft component comprises an interior surface and an exterior surface, end portions of the interior surface of the first graft component being attached to end portions of the second graft component, and the stent structure is attached to the exterior surface of the first graft component.

3. The prosthesis of claim 2, wherein the first graft component is configured to stretch in response to a force applied to at least one of the first graft component, the second graft component, and the stent structure.

4. The prosthesis of claim 3, wherein the first graft component is configured to maintain the gap between the first graft component and the second graft component in response to the force applied to at least one of the first graft component, the second graft component, and the stent structure.

5. The prosthesis of claim 1, wherein the first graft component is configured to mitigate against the stent structure contacting the second graft component.

6. The prosthesis of claim 1, wherein the first graft component is configured to stretch in response to a pressure, and the pressure originates from at least one of: within the second graft component, between the first graft component and the second graft component, and external to the first graft component.

7. The prosthesis of claim 6, wherein the second graft component includes an interior surface and an exterior surface, the first graft component comprises an interior surface and an exterior surface, and the interior surface of the second graft component is configured to form a blood flow lumen, and the exterior surface of the first graft component is configured to contact a vessel wall.

8. The prosthesis of claim 1, wherein the first graft component, the second graft component, and the stent structure are configured to conform to a shape of a vessel wall, and the first graft component is configured to stretch and maintain the gap between the first graft component and the second graft component in response conforming to the shape of the vessel wall.

9. The prosthesis of claim 1, wherein end portions of the first graft component are attached to end portions of the second graft component, and an intermediate portion of the first graft component between the end portions of the first graft component and the end portions of the second graft component is configured to move independently of the second graft component.

10. The prosthesis of claim 1, wherein at least one of the first mass per area and the first tensile strength are less than the second mass per area and the second tensile strength.

11. The prosthesis of claim 10, wherein the first mass per area and the first tensile strength are less than the second mass per area and the second tensile strength.

12. The prosthesis of claim 1, wherein the first graft component includes a first opening, and the second graft component includes a second opening, and further comprising a portal bridge arranged between the first opening and the second opening.

13. A prosthesis comprising:
a first graft component;
a second graft component arranged within the first graft component, the second graft component comprising a first end portion, a second end portion, and an intermediate portion, the intermediate portion having a diameter less than a diameter of at least one of the first end portion and the second end portion;
a portal bridge arranged between a first opening in the first graft component and a second opening in the second graft component;
a gap arranged between the first graft component and the second graft component; and
a stent structure arranged with the first graft component.

14. The prosthesis of claim 13, wherein the portal bridge comprises a graft structure connecting the first opening and the second opening.

15. The prosthesis of claim 14, wherein the portal bridge is free of stent or support components.

16. The prosthesis of claim 13, wherein the first graft component, the second graft component, and the stent structure are configured to conform to a shape of a vessel wall, and the first graft component is configured to stretch and maintain the gap between the first graft component and the second graft component in response conforming to the shape of the vessel wall.

17. The prosthesis of claim 16, wherein the portal bridge is configured to accept a side branch device therethrough and facilitate placement of the branched device within a side branch vessel.

18. The prosthesis of claim 17, wherein the portal bridge is configured to self-deploy and open to accept the side branch device therethrough and facilitate placement of the branched device within the side branch vessel.

19. The prosthesis of claim 13, further comprising at least another portal bridge arranged between another opening in the first graft component and another opening in the second graft component.

20. The prosthesis of claim 13, wherein the second graft component includes an interior surface and an exterior surface, the first graft component comprises an interior surface and an exterior surface, and the interior surface of the second graft component includes a smooth transition to an interior surface of the portal bridge.

21. A prosthesis comprising:
- a first graft component including a first mass per area and a first tensile strength;
- a second graft component arranged within the first graft component and coupled thereto at end portions of the second graft component and end portions of the first graft component, the second graft component including a second mass per area and a second tensile strength, and at least one of the first mass per area and the first tensile strength differs from at least one of the second mass per area and the second tensile strength;
- a space formed by the first graft component and the second graft component and arranged between the end portions of the first graft component and the end portions of the second component; and
- a stent structure arranged with the first graft component.

22. The prosthesis of claim 21, wherein the first graft component includes a first diameter, and at least a portion of the second graft component includes a second diameter, and the second diameter is less than the first diameter.

23. The prosthesis of claim 22, wherein the end portions of the second graft component include a third diameter, and an intermediate portion of the second graft component includes the second diameter, and the second diameter is less than the third diameter.

24. The prosthesis of claim 23, wherein the end portions of the second graft component tapered toward the intermediate portion of the second graft component from the third diameter to the second diameter.

25. The prosthesis of claim 21, wherein the second graft component comprises a shape that includes at least one of a dog bone shape and an hourglass shape.

* * * * *